(12) United States Patent
Legroux et al.

(10) Patent No.: US 7,943,769 B2
(45) Date of Patent: May 17, 2011

(54) FLUORINATED DERIVATIVE OF QUINOLIN-2(1H)-ONE, METHOD FOR PREPARING THE SAME AND USE THEREOF AS A SYNTHESIS INTERMEDIATE

(75) Inventors: Didier Legroux, Paris (FR); Veronique Moragues, Paris (FR); Jose Ruiz-Montes, Paris (FR); Laurent Salle, Paris (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/483,288

(22) Filed: Jun. 12, 2009

(65) Prior Publication Data

US 2010/0094005 A1 Apr. 15, 2010

Related U.S. Application Data

(63) Continuation of application No. PCT/FR2007/002027, filed on Dec. 10, 2007.

(30) Foreign Application Priority Data

Dec. 12, 2006 (FR) .................................... 06 10802

(51) Int. Cl.
*C07D 495/04* (2006.01)
(52) U.S. Cl. ....................................................... 544/363
(58) Field of Classification Search .................... None
See application file for complete search history.

(56) References Cited

U.S. PATENT DOCUMENTS 5,958,924 A * 9/1999 McCort et al. ........... 514/253.04

FOREIGN PATENT DOCUMENTS

| EP | 0574313 | 12/1993 |
|---|---|---|
| EP | 9710238 | 3/1997 |
| EP | 1078928 | 2/2001 |
| FR | 2738823 | 9/1995 |

* cited by examiner

*Primary Examiner* — Emily Bernhardt
(74) *Attorney, Agent, or Firm* — Scully, Scott, Murphy & Presser, P.C.

(57) ABSTRACT

The invention relates to a fluorinated derivate of quinolin-2 (1H)-one (I), to a method for preparing the same, and to the use thereof as an intermediate in the synthesis of 7-fluoro-2-oxo-4-[2-[4-[thieno[3,2-c]pyridine-4-yl)piperazin-1-yl] ethyl]-1,2-dihydro-quinolin-1-acetamide. The invention also relates to the pharmaceutically acceptable salts thereof.

19 Claims, No Drawings

FLUORINATED DERIVATIVE OF QUINOLIN-2(1H)-ONE, METHOD FOR PREPARING THE SAME AND USE THEREOF AS A SYNTHESIS INTERMEDIATE

The present invention relates to a novel fluoro derivative of quinolin-2(1H)-one, to the process for the preparation thereof and to the use thereof as synthesis intermediate, in particular for the synthesis of 7-fluoro-2-oxo-4-[2-[4-(thieno[3,2-c]pyridin-4-yl)piperazin-1-yl]ethyl]-1,2-dihydroquinoline-1-acetamide.

7-Fluoro-2-oxo-4-[2-[4-(thieno[3,2-c]pyridin-4-yl)piperazin-1-yl]ethyl]-1,2-dihydroquinoline-1-acetamide, hereinafter referred to as "compound (II)", is described in Patent EP 0850235.

This compound is known for its therapeutic value, and in particular as a serotonin antagonist, more particularly $5HT_{1B}$ receptor and $5HT_{2A}$ receptor antagonists; it can be used in the treatment and prevention of various forms of pathologies involving serotonin, such as arterial, venous, pulmonary, portal, renal or ocular hypertension, cardiac, renal, ocular or cerebral ischaemia or ischaemia of the lower limbs, heart failure, myocardial infarction, angina, coronary or peripheral vasospasms, thromboses (alone or as adjuvant to thrombolysis), arteritis, intermittent claudication, restenosis after angioplasty and various pathological states associated with atherosclerosis, with microcirculation disorders or with pulmonary dysfunction. It can also be used, alone or in combination with other substances, in vascular graft procedures.

The process for preparing compound (II), as described in Patent EP 0850235, is the following:

1) reaction of 4-(acetyloxy)-2H,3H-pyran-2,6-dione with 3-fluoroaniline, at ambient temperature and in pure acetic acid, so as to obtain, after washing and drying, 3-(acetyloxy)-5-[(3-fluorophenyl)amino]-5-oxopent-2-enoic acid, 2) cyclization of the compound previously obtained, in the presence of an inorganic acid such as concentrated sulphuric acid and so as to obtain 4-(acetic acid)-7-fluoroquinolin-2(1H)-one (compound (III) hereinafter), 3) esterification of the acid thus obtained so as to obtain methyl-7-fluoro-quinolin-2(1H)-one 4-acetate, 4) reduction of the ester previously obtained so as to obtain 7-fluoro-4-(2-hydroxyethyl)quinolin-2(1H)-one, 5) activation of this alcohol by reaction with thionyl chloride so as to obtain the chlorinated derivative, 4-(2-chloroethyl)-7-fluoroquinolin-2(1H)-one, 6) reaction of the chlorinated compound thus obtained with 4-(piperazin-1-yl)thieno[3,2-c]pyridine (compound (IV) hereinafter) so as to obtain 7-fluoro-4-[2-[4-(thieno[3,2-c]pyridin-4-yl)piperazin-1-yl]ethyl]quinolin-2(1H)-one, 7) reaction of the compound thus obtained with bromoacetamide in tetrahydrofuran in the presence of potassium hydroxide and of tetrabutylammonium bromide, resulting in 7-fluoro-2-oxo-4-[2-[4-(thieno[3,2-c]pyridin-4-yl)piperazin-1-yl]ethyl]-1,2-dihydroquinoline-1-acetamide (compound (II) hereinafter).

The inventors gave themselves the aim of achieving a novel process for synthesizing compound (II) using a novel synthesis intermediate.

A subject of the invention is thus the compound of formula (I):

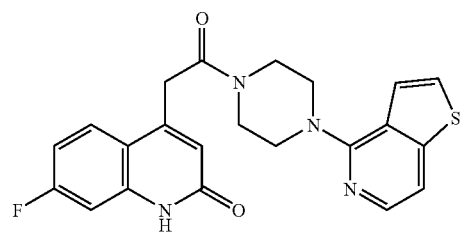

and pharmaceutically acceptable salts thereof.

In fact, the compound of formula (I) can exist in the form of a base or in a form salified with acids or bases, in particular pharmaceutically acceptable acids or bases. Such addition salts are part of the invention.

These salts are advantageously prepared with pharmaceutically acceptable acids, but the salts of other acids that are useful, for example, for purifying or isolating the compounds of formula (I) are also part of the invention.

The compound of formula (I) can also exist in the form of hydrates or of solvates, i.e. in the form of associations or combinations with one or more molecules of water or with a solvent. Such hydrates and solvates are also part of the invention.

This compound is of particular use in the synthesis of quinolin-2(1H)-one derivatives, especially for the synthesis of compound (II), as described in Patent EP 0850235, having the following structural formula:

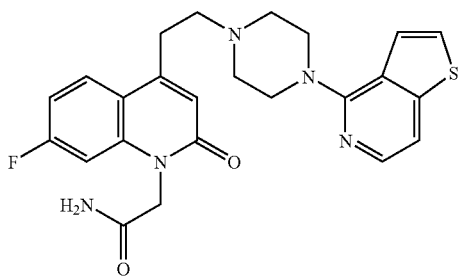

According to the seven-stage process described in EP 0850235, compound (II) is recovered with a maximum chemical yield of 16% from the starting products, i.e. 4-(acetyloxy)-2H,3H-pyran-2,6-dione and 3-fluoroaniline. Moreover, the reaction in which 7-fluoro-4-(2-hydroxyethyl)quinolin-2(1H)-one is chlorinated (stage 5), described above, is not very selective and leads to the formation, up to 25% in molar amount, of a dichlorinated side compound represented below:

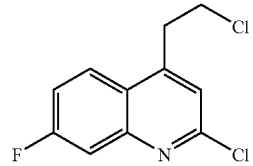

Consequently, the development of a process for preparing compound (II), which comprises a reduced number of steps and provides a sufficient yield of desired compound, remains of unquestionable advantage.

Now, it has been discovered that it is possible to use a new reaction intermediate, 7-fluoro-4-[2-[4-(thieno[3,2-c]pyridin-4-yl)piperazin-1-yl]-2-oxoethyl]quinolin-2(1H)-one, known as compound (I), for synthesizing compound (II). The novel process using intermediate (I) makes it possible to synthesize compound (II) in a reduced number of stages compared with the known prior process, and with a greatly improved yield.

According to the invention, compound (I) can be synthesized according to FIGURE 1.

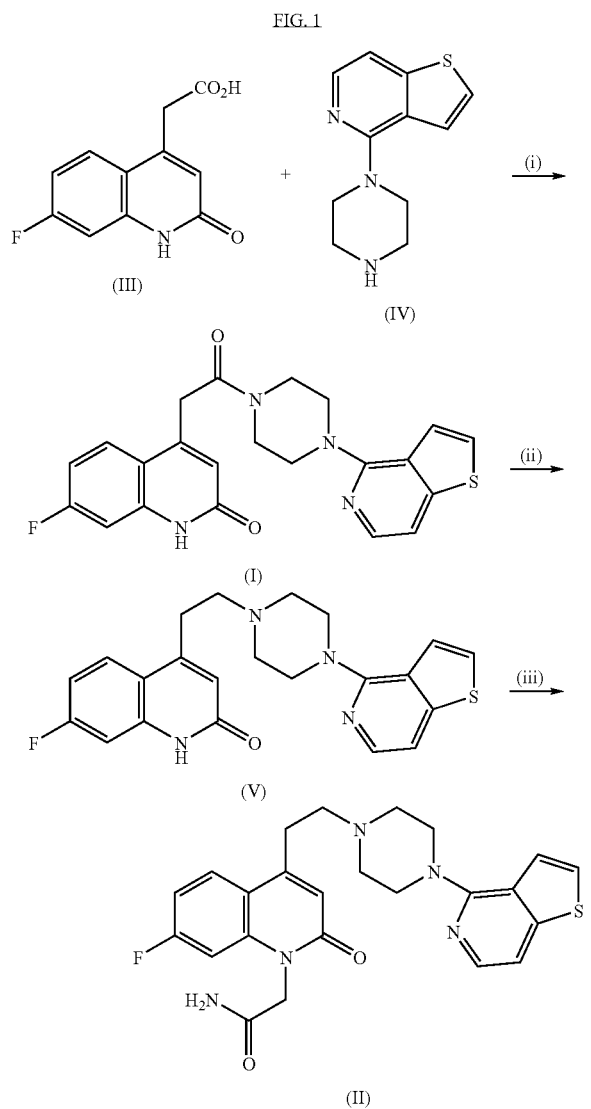

Compound (I) can be obtained, in a stage (i), by reacting, in an aprotic polar solvent such as tetrahydrofuran (THF), methyltetrahydrofuran, toluene, acetonitrile, N-methylpyrrolidone (NMP) or dimethylformamide (DMF), 4-(acetic acid)-7-fluoroquinolin-2(1H)-one (III) with 4-(piperazin-1-yl)thieno[3,2-c]pyridine (IV) in the presence of a coupling agent, present in excess, such as pivaloyl chloride, thionyl chloride, ethyl chloroformate, isobutyl chloroformate, preferably carbonyldiimidazole.

The starting compounds (III) and (IV) are commercially available or described in the literature, in particular in Application EP 0850235, or can be prepared according to methods which are described therein or which are known to those skilled in the art.

In stage (ii), compound (I) is subsequently reduced with an alkali metal hydride in a polar or an apolar solvent such as, for example, lithium aluminium hydride in tetrahydrofuran, methyltetrahydrofuran, toluene, zinc borohydride ($ZnBH_4$) in tetrahydrofuran, sodium borohydride in the presence of a Lewis acid such as $TiCl_4$ or $AlCl_3$ or borane according to conditions known to those skilled in the art, preferably lithium aluminium hydride in tetrahydrofuran; the 7-fluoro-4-[2-[4-[thieno[3,2-c]pyridin-4-yl]piperazin-1-yl]ethyl]quinolin-2(1H)-one (V) previously mentioned during the synthesis of compound (II) described in EP 0850235, is obtained.

In stage (iii), the secondary amine is subsequently alkylated using an electrophilic or alkylating agent, for example of formula halogen-$CH_2$—CO—$NH_2$, such as alkyl halides of the 2-bromoacetamide or 2-chloroacetamide type, preferably 2-chloroacetamide, in the presence of a base such as potassium carbonate, in an aprotic polar solvent such as tetrahydrofuran, potassium hydroxide or sodium hydroxide, in dimethylformamide, in the presence or absence of a phase-transfer catalyst, such as tetrabutylammonium bromide. The synthesis compound (II) is obtained.

Thus, according to the novel process in accordance with the invention, compound (V) is obtained from 4-(acetic acid)-7-fluoroquinolin-2(1H)-one (III) and from 4-(piperazin-1-yl)thieno[3,2-c]pyridine (IV) in two stages, with yields of 99.3% and 64.6% respectively for each stage, and with a yield for these two stages of 64%. In comparison with Patent EP 0850235, compound (V) is obtained in four stages from compound (III), with an overall yield of 30.5%.

The examples which follow illustrate the invention without limiting it. The microanalyses and the IR, NMR and mass spectra confirm the structure of the compounds obtained.

EXAMPLE 1

Synthesis of Compound (I)

1. Synthesis of the Starting Products 1.1. 4-(Piperazin-1-yl)thieno[3,2-c]pyridine (IV)

1 kg of 4-chlorothieno[3,2-c]pyridine (1 eq.), 1.5 kg of piperazine (3 eq.) and 8 l of 1-pentanol or of isoamyl alcohol are introduced into a reactor. The mixture is refluxed for 5 h and cooled, and the piperazine hydrochloride formed is filtered. 2.4 l of water are added to the filtrate and the mixture is acidified with concentrated hydrochloric acid. After separation by settling out, the aqueous phase is brought to a basic pH with a solution of 2.3 l of 30% sodium hydroxide and 2.6 l of water, and then extracted with two times 1.3 l of toluene. The toluenic phase is concentrated by half and 3.5 l of methylcyclohexane are added. The mixture is cooled to 0° C. and filtered and the product obtained is dried under vacuum at 50° C. A pale yellow powder of compound (IV) is obtained.
Yield: 74%
Analyses: HPLC=99.2%

1.2. 4-(Acetic acid)-7-fluoroquinolin-2(1H)-one (III)

As described in Patent EP 0850235, 62.32 kg (366.3 mol) of 4-(acetyloxy)-2H,3H-pyran-2,6-dione are added in small portions to a stirred solution of 40.77 kg (366.9 mol) of 3-fluoroaniline in 125 l of pure acetic acid. The reaction medium is stirred for two hours at 30° C., left to cool to ambient temperature and diluted in 375 l of demineralized water. The solid obtained is recovered, spin-filter-dried, washed thoroughly with water and dried in an oven under vacuum (40° C.) for 48 hours.

67.38 kg of 3-(acetyloxy)-5-[(3-fluorophenyl)amino]-5-oxopent-2-enoic acid in the form of a powder are obtained.

Yield: 65.4%

Analyses: melting point=117° C.

67.38 kg (239.6 mol) of 3-(acetyloxy)-5-[(3-fluorophenyl)amino]-5-oxopent-2-enoic acid are poured, in small portions, into 186 l of concentrated sulphuric acid at 15° C. with vigorous stirring, and then the reaction medium is heated at 100° C. for 90 minutes. After cooling, this solution is slowly poured into 371 l of demineralized water at 15° C. The solid thus obtained is filtered off. It is washed with water. The moist product is suspended in 154 l of DMF and the mixture is stirred vigorously for one hour at 30° C. The product is filtered and washed with DMF. Compound (III) is obtained.

Yield: 82.3%

Analyses: HPLC=97.3%

2. 7-Fluoro-4-[2-[4-(thieno[3,2-c]pyridin-4-yl)piperazin-1-yl]-2-oxoethyl]quinolin-2(1H)-one (I)

56.95 kg (1 eq.) of 4-(acetic acid)-7-fluoroquinolin-2(1H)-one (III), followed by 850 l of THF, are introduced into a reactor. 49.2 kg (1.17 eq.) of carbonyldiimidazole are then added with stirring. The mixture is heated at 45° C. for 17 h, and then a solution of 56.9 kg (1 eq.) of 4-(piperazin-1-yl)thieno[3,2-c]pyridine (IV) in 114 l of THF is added. The mixture is stirred at 60° C. for twelve hours. It is cooled to 20° C., and filtration and washing with THF are carried out. The product (I) is not dried and it is directly used in the following stage.

Yield: 99.3%

Analyses: HPLC=95.2%

$^1$H NMR (DMSO, 300 MHz): δ 3.50 (m, 4H); 3.75 (m, 4H); 4.05 (s, 2H); 6.37 (s, 1H); 7.05 (m, 2H); 7.5 (m, 2H); 7.70 (m, 1H); 7.79 (d, 1H); 8.04 (d, 1H); 11.77 (s, 1H).

EXAMPLE 2

Synthesis of 7-fluoro-2-oxo-4-[2-[4-(thieno[3,2-c]pyridin-4-yl)piperazin-1-yl]ethyl]-1,2-dihydroquinoline-1-acetamide (II)

1. 7-Fluoro-4-[2-[4-[thieno[3,2-c]pyridin-4-yl]piperazin-1-yl]ethyl]quinolin-2(1H)-one (V)

107.7 kg (1 eq.) of intermediate 7-fluoro-4-[2-[4-(thieno[3,2-c]pyridin-4-yl)piperazin-1-yl]-2-oxoethyl]quinolin-2(1H)-one (I), followed by 323 l of THF, are introduced, in thirty minutes at 10° C., into a suspension of 22.2 kg (2.3 eq.) of lithium aluminium hydride in 580 l of tetrahydrofuran, in a reactor. The mixture is stirred for three hours at ambient temperature and then, after verification that the reaction is complete, the mixture is cooled and 21.5 l of water, 21.5 l of 4N sodium hydroxide and 180 l of water are added successively without the temperature exceeding 15° C. The mixture is stirred for one hour and the inorganic salts are filtered off. The mixture is concentrated to three volumes of THF and run into 1400 l of water. The mixture is filtered and a paste is re-formed in 1000 l of a water/THF mixture: 3/7. The product is dried under vacuum at 50° C. Compound (V) is obtained.

Yield: 64.6%

Analyses: HPLC=98.5%

2. 7-Fluoro-2-oxo-4-[2-[4-(thieno[3,2-c]pyridin-4-yl)piperazin-1-yl]ethyl]1,2-di-hydroquinoline-1-acetamide (II)

66.9 kg of 7-fluoro-4-[2-[4-[thieno[3,2-c]pyridin-4-yl]piperazin-1-yl]ethyl]-quinolin-2(1H)-one (V), 18.4 kg of 2-chloroacetamide (1.2 eq.), 51.5 kg of potassium carbonate (2 eq.) and 335 l of DMF are introduced into a reactor. The mixture is stirred at 50° C. for twenty hours and then cooled to 25° C. and 1000 l of water are added. The suspension obtained is filtered and washed with water and a paste is re-formed in 307 l of ethanol. The solid is filtered off. 60.7 kg, estimated on a dry basis, of a white solid (II) are obtained.

What is claimed is:

1. A compound according to formula (I):

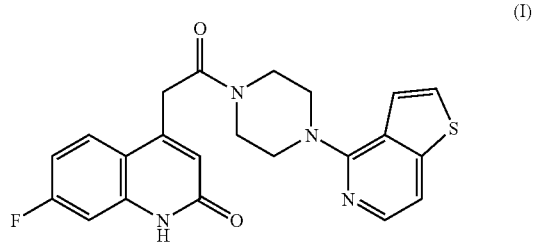

(I)

or a salt thereof.

2. A compound according to claim 1, wherein said compound is: 7-Fluoro-4-[2-[4-(thieno[3,2-c]pyridin-4-yl)piperazin-1-yl]-2-oxoethyl]quinolin-2(1H)-one.

3. A compound according to claim 1, wherein said compound is in the form of a salt.

4. A compound according to claim 3, wherein said compound is in the form of a pharmaceutically acceptable salt.

5. A process for preparing 7-fluoro-4-[2-[4-(thieno[3,2-c]pyridin-4-yl)piperazin-1-yl]-2-oxoethyl]quinolin-2(1H)-one, said process comprising the step of reacting 4-(acetic acid)-7-fluoroquinolin-2(1H)-one with 4-(piperazin-1-yl)thieno[3,2-c]pyridine.

6. The process according to claim 5, wherein said reaction occurs in the presence of an aprotic polar solvent.

7. The process according to claim 6, wherein said reaction occurs in the presence of tetrahydrofuran, methyltetrahydrofuran, toluene, acetonitrile, N-methylpyrrolidone or dimethylformamide.

8. The process according to claim 5, wherein said reaction occurs in the presence of a coupling agent.

9. The process according to claim 8, wherein said coupling agent is present in excess.

10. The process according to claim 8, wherein said reaction occurs in the presence of pivaloyl chloride, thionyl chloride, ethyl chloroformate, isobutyl chloroformate or carbonyldiimidazole.

11. The process according to claim 10, wherein said reaction occurs in the presence of carbonyldiimidazole.

12. A process for preparing 7-fluoro-2-oxo-4-[2-[4-[thieno[3,2-c]pyridin-4-yl]piperazin-1-yl]ethyl]-1,2-dihydroquinoline-1-acetamide, said process comprising the step of reducing 7-fluoro-4-[2-[4-(thieno[3,2-c]pyridin-4-yl)piperazin-1-yl]-2-oxoethyl]quinolin-2(1H)-one to form 7-fluoro-4-[2-[4-(thieno[3,2-c]pyridin-4-yl)piperazin-1-yl]ethyl]quinolin-2(1H)-one followed by alkylating said 7-fluoro-4-[2-[4-(thieno[3,2-c]pyridin-4-yl)piperazin-1-yl]ethyl]quinolin-2(1H)-one using halogen-$CH_2$—CO—$NH_2$ to form 7-fluoro- 2-oxo-4-[2-[4-[thieno[3,2-c]pyridin-4-yl]piperazin-1-yl] ethyl]-1,2-dihydroquinoline-1-acetamide.

13. The process according to claim 12, wherein said reduction occurs in a polar or an apolar solvent in the presence of an alkali metal hydride or borane.

14. The process according to claim 13, wherein said reduction occurs in the presence of lithium aluminium hydride, zinc borohydride or sodium borohydride.

15. The process according to claim 14, wherein said reduction occurs in the presence of sodium borohydride and a Lewis acid.

16. The process according to claim 15, wherein said Lewis acid is $TiCl_4$ or $AlCl_3$.

17. The process according to claim 13, wherein said solvent is selected from the group consisting of tetrahydrofuran, methyltetrahydrofuran, and toluene.

18. The process according to claim 13, wherein said reduction occurs in the presence of lithium aluminium hydride and said solvent comprises tetrahydrofuran.

19. A process for preparing 7-fluoro-2-oxo-4-[2-[4-[thieno[3,2-c]pyridin-4-yl]piperazin-1-yl]ethyl]-1,2-dihydroquinoline-1-acetamide, said process comprising the steps of:
   (i) reacting 4-(acetic acid)-7-fluoroquinolin-2(1H)-one with 4-(piperazin-1-yl)thieno[3,2-c]pyridine to form 7-fluoro-4-[2-[4-(thieno[3,2-c]pyridin-4-yl)piperazin-1-yl]-2-oxoethyl]quinolin-2(1H)-one;
   (ii) reducing said 7-fluoro-4-[2-[4-(thieno[3,2-c]pyridin-4-yl)piperazin-1-yl]-2-oxoethyl]quinolin-2(1H)-one to form 7-fluoro-4-[2-[4-(thieno[3,2-c]pyridin-4-yl)piperazin-1-yl]ethyl]quinolin-2(1H)-one; and
   (iii) alkylating said 7-fluoro-4-[2-[4-(thieno[3,2-c]pyridin-4-yl)piperazin-1-yl]ethyl]quinolin-2(1H)-one by means of 2-bromoacetamide or 2-chloroacetamide.

* * * * *